United States Patent
Schafer et al.

(10) Patent No.: US 10,251,409 B2
(45) Date of Patent: Apr. 9, 2019

(54) MIXTURES OF MATTER

(71) Applicants: Uwe Schafer, Ottenstein (DE);
Gerhard Krammer, Holzminden (DE);
Gerald Glaubitz, Höxter (DE);
Thomas Riess, Holzminden (DE);
Jakob Ley, Holzminden (DE); Susanne Paetz, Höxter (DE)

(72) Inventors: Uwe Schafer, Ottenstein (DE);
Gerhard Krammer, Holzminden (DE);
Gerald Glaubitz, Höxter (DE);
Thomas Riess, Holzminden (DE);
Jakob Ley, Holzminden (DE); Susanne Paetz, Höxter (DE)

(73) Assignee: SYMRISE AG, Holzminden (DE)

( * ) Notice: Subject to any disclaimer, the term of this patent is extended or adjusted under 35 U.S.C. 154(b) by 0 days.

(21) Appl. No.: 15/032,843

(22) PCT Filed: Oct. 26, 2014

(86) PCT No.: PCT/EP2014/072928
§ 371 (c)(1),
(2) Date: Apr. 28, 2016

(87) PCT Pub. No.: WO2015/062998
PCT Pub. Date: May 7, 2015

(65) Prior Publication Data
US 2016/0295892 A1 Oct. 13, 2016

(30) Foreign Application Priority Data
Oct. 31, 2013 (EP) .................................... 13191008

(51) Int. Cl.
A23G 4/00 (2006.01)
A23G 4/10 (2006.01)
A23C 9/13 (2006.01)
A23C 9/154 (2006.01)
A23L 2/60 (2006.01)
A23G 3/36 (2006.01)
A23G 4/06 (2006.01)
A61Q 11/00 (2006.01)
A61K 8/60 (2006.01)
A61K 8/73 (2006.01)
A23L 9/10 (2016.01)
A23L 27/00 (2016.01)
A23L 27/20 (2016.01)
A23L 27/30 (2016.01)
A23G 3/42 (2006.01)
A23L 1/187 (2006.01)
A23L 1/22 (2006.01)
A23L 1/226 (2006.01)
A23L 1/236 (2006.01)

(52) U.S. Cl.
CPC ............. *A23G 4/10* (2013.01); *A23C 9/1307* (2013.01); *A23C 9/1544* (2013.01); *A23G 3/36* (2013.01); *A23G 3/42* (2013.01); *A23G 4/06* (2013.01); *A23L 1/187* (2013.01); *A23L 1/22091* (2013.01); *A23L 1/22657* (2013.01); *A23L 1/2363* (2013.01); *A23L 1/2365* (2013.01); *A23L 2/60* (2013.01); *A23L 9/10* (2016.08); *A23L 27/204* (2016.08); *A23L 27/30* (2016.08); *A23L 27/33* (2016.08); *A23L 27/35* (2016.08); *A23L 27/36* (2016.08); *A23L 27/88* (2016.08); *A61K 8/602* (2013.01); *A61K 8/732* (2013.01); *A61Q 11/00* (2013.01); *A23V 2002/00* (2013.01); *A61K 2800/592* (2013.01)

(58) Field of Classification Search
CPC ... A23G 4/10; A23G 4/06; A23G 3/36; A23G 3/42; A23C 9/1307; A23C 9/1544; A23L 2/60; A23L 9/10; A23L 27/88; A23L 27/204; A23L 27/30; A23L 27/33; A23L 27/35; A23L 27/36; A23L 1/187; A23L 1/22091; A23L 1/2657; A23L 1/2363; A23L 1/2365; A61Q 11/00; A61K 8/602; A61K 8/732; A61K 2800/592; A23V 2002/00
USPC ................................. 426/531, 534, 536, 548
See application file for complete search history.

(56) References Cited

U.S. PATENT DOCUMENTS 8,574,656 B2 * 11/2013 Abelyan ................... A21D 2/36
426/548
8,679,461 B2 * 3/2014 Ley .......................... A61K 8/02
424/49

(Continued)

FOREIGN PATENT DOCUMENTS

EP 2 215 914 A1 8/2010
EP 2 340 719 A1 7/2011

(Continued)

OTHER PUBLICATIONS

Japanese Office Action dated Aug. 27, 2018 for corresponding Japanese Application No. 2016-522036.

Primary Examiner — Leslie A Wong
(74) Attorney, Agent, or Firm — Polsinelli PC

(57) ABSTRACT

Suggested is a mixture of matter, comprising: (a) steviol glycosides, (b) starch degradation products and (c) one or more phenolic sweetness-enhancing aroma substances selected from the group formed by hesperetin, phloretin, 1-(2,4-dihydroxyphenyl)-3-(3-hydroxy-4-methoxyphenyl) propan-1-one, 7,3-dihydroxy-4'-methoxyflavan and 5-hydroxy-4-(4-hydroxy-3-methoxyphenyl)-7-methoxy-2-chromanone. On condition that components (a+b) and (c) are present in a ratio by weight of from 1.99 to 99:1.

18 Claims, No Drawings

(56) References Cited

U.S. PATENT DOCUMENTS

| | | | |
|---|---|---|---|
| 8,778,987 B2* | 7/2014 | Ley | C07C 49/83 |
| | | | 426/3 |
| 8,962,058 B2* | 2/2015 | Prakash | A23L 2/60 |
| | | | 426/541 |
| 9,000,054 B2* | 4/2015 | Tachdjian | A23L 1/22678 |
| | | | 426/544 |
| 9,131,719 B2* | 9/2015 | Backes | A23L 1/2363 |
| 9,198,451 B2* | 12/2015 | Riess | A23L 1/2366 |
| 2010/0166679 A1 | 7/2010 | Abelyan et al. | |
| 2011/0076239 A1 | 3/2011 | Reichelt et al. | |

FOREIGN PATENT DOCUMENTS

| | | |
|---|---|---|
| EP | 2 359 702 A1 | 8/2011 |
| EP | 2 529 633 A1 | 12/2012 |
| EP | 2 628 398 A1 | 8/2013 |
| JP | 2008-271836 A | 11/2008 |
| WO | WO-2012/128775 A1 | 9/2012 |

\* cited by examiner

MIXTURES OF MATTER

This application is a 371 of PCT/EP2014/072928 Filed Oct. 26, 2014.

FIELD OF INVENTION

The invention is located in the field of foods and relates to novel mixtures of matter which firstly are aroma substances having an improved sweetening activity and at the same time improve the solubility of other aroma substances in the finished preparations.

STATE OF THE ART

*Stevia* is recovered from the leaves of the plant *Stevia rebaudiana* and is a complex mixture of various steviol glycosides. *Stevia* extracts are used as calorie-free sweeteners, wherein pure *Stevia* has 450 times the sweetening power of sugar. The *Stevia* plant is originally located in South America, where the sweetening power thereof has long been known to the original inhabitants. Nowadays, the plant is grown on large scales in Japan and China. In the European Union, *Stevia* has been permitted since 2011 as food additive E 960 even if currently a maximum of 30 of the sugar of a product may be replaced by *Stevia*.

Products which contain steviol glycosides as sweetener are adequately known from the prior art. Activities to increase the content in steviosides by enrichment methods and to enrich individual isomers in this process are likewise known. For instance, in the two international patent applications WO 2012 112180 A1, WO 2012 128775 A1 and WO 2012 129451 A1 (Pure Circle) mixtures of rebaudiosides and steviosides and also use thereof as sweeteners are described, for example.

WO 2013 096420 A1 (TCCC) relates to a chromatographic method for purifying steviol glycosides.

EP 2340729 A1 (SYMRISE) discloses in Example 9 a soft drink composition comprising sugar syrup, Rebaudioside A, phloretin and hesperetin.

EP 2359702 A1 (SYMRISE) refers to a method for solubilizing polyphenols in aqueous solutions. Example 6 discloses a composition comprising inter alia Rebaudioside A, hesperetin and sugar syrup.

Nevertheless, *Stevia* quality grades that are present on the market are distinguished in that they overall have a bitter, sometimes astringent aftertaste, which still makes broad use thereof more difficult. The solubility of steviol glycosides in foods, especially in liquid products, is also not satisfactory.

The object of the present invention was therefore not only to round off the flavour of the imperfect sensory profile of steviol glycosides, but also, as a sub-object, to simultaneously improve the frequently inadequate solubility of aroma substances in general and steviol glycosides in particular in the finished end products.

DESCRIPTION OF THE INVENTION

The invention relates to mixtures of matter, comprising
(a) steviol glycosides,
(b) starch degradation products and
(c) one or more phenolic sweetness-enhancing aroma substances selected from the group formed by hesperetin, phloretin, 1-(2,4-dihydroxyphenyl)-3-(3-hydroxy-4-methoxyphenyl)propan-1-one, 7,3-dihydroxy-4'-methoxyflavan and 5-hydroxy-4-(4-hydroxy-3-methoxyphenyl)-7-methoxy-2-chromanone, on condition that components (a+b) and (c) are present in a ratio by weight of from 1.99 to 99:1

Surprisingly, it has been found that the mixtures based on the components (a) and (c) have an enhanced sweetening activity and are particularly suitable for rounding off and optimizing the taste sensory property of foods. In particular, in the combination having the starch breakdown products and hesperetin, the bitter to pungent aftertaste is masked. At the same time, the mixtures are distinguished not only themselves by an improved solubility, they are unexpectedly also able to enhance significantly the solubility of other aroma substances in the finished end products.

Steviol Glycosides

Steviol glycosides are recovered from the plant *Stevia rebaudiana* ("sugar plant", also "sweet herb of Paraguay") and are a mixture of matter, which is used as sweetener. It consists principally of diterpene glycosides such as stevioside, rebaudioside A and seven to ten further isomers and homologues such as rebaudiosides B, C and D and steviolbioside.

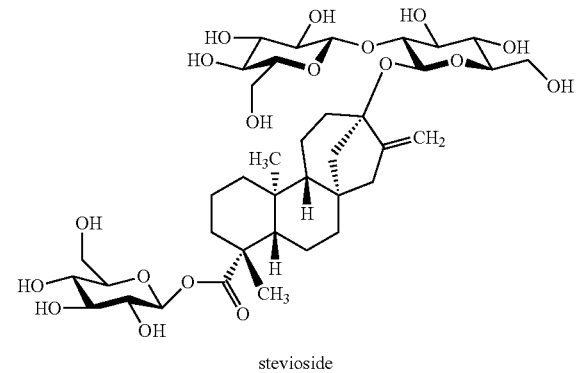

stevioside

The fractions of the steviol glycosides present differ according to area of cultivation and plant variety. Further differences in fractions result, since manufacturers of table sweetener-based on steviol glycoside usually increase the rebaudioside-A fraction because of the sugar-like taste. The liquorice-like taste of the plant is counteracted in the production of the sweetener mixture by isolating the sweetening components and subsequent compounding. *Stevia* products can—as pure rebaudioside A—have a sweetening power up to 450 times that of sugar.

Steviol glycosides which are preferred in the context of the present invention have at least 2, preferably at least 3, and in particular 2 to 6 glucose units, wherein in this case at least one or more are preferably present as alpha-1,4-linked D-glucose units.

Particular preference, however, is given to steviol glycosides which comply with the following composition:

(a1) about 1 to about 50, preferably about 1 to 15, % by weight rebaudiosides A or isomers thereof, wherein one or more of the rebaudioside A isomers can be present in relation to rebaudioside A at 100:1 to 1:100, (a2) about 0.1 to about 30, preferably about 1 to 15, % by weight rebaudiosides B or isomers thereof, wherein one or more of the rebaudioside B isomers can be present in relation to rebaudioside B at 100:1 to 1:100, (a3) about 1 to about 50, preferably about 1 to about 15, % by weight rebaudiosides C or isomers thereof, wherein one or more of the rebaudioside C isomers can be present in relation to rebaudioside C at 100:1 to 1:100, (a4) about 1 to about 25, preferably about 1 to about 15, % by weight rebaudiosides D or isomers thereof, wherein one or more of the rebaudioside D isomers can be present in relation to rebaudioside D at 100:1 to 1:100,
(a5) about 1 to about 25, preferably about 1 to about 20, % stevioside or isomers thereof, wherein one or more of the stevioside isomers can be present in relation to stevioside at 100:1 to 1:100, and
(a6) about 1 to about 5, preferably about 2 to about 4, % by weight steviolbioside or isomers thereof, wherein one or more of the steviolbioside isomers can be present in relation to steviolbioside at 100:1 to 1:100,
(a7) optionally also 1 to 50% by weight, preferably 1 to 10%, rubusoside or isomers thereof, wherein one or more of the rubusoside isomers can be present in relation to rubusoside at 100:1 to 1:100,
(a8) optionally also 1 to 15% by weight rebaudioside E or isomers thereof, wherein one or more of the rebaudioside E isomers can be present in relation to rebaudioside E at 100:1 to 1:100,
(a9) optionally also 1 to 15% by weight rebaudioside F or isomers thereof, wherein one or more of the rebaudioside F isomers can be present in relation to rebaudioside F at 100:1 to 1:100,
(a9) optionally also 1 to 15% by weight dulcoside A or isomers thereof, wherein one or more of the dulcoside A isomers can be present in relation to dulcoside A at 100:1 to 1:100,
(a10) and 1 to 90, preferably 20 to 80%, higher steviol glycosides having 5 to 50, preferably 6 to 16 glycosidic units can be present
with the proviso that the indications of quantity total 100% by weight.

Particularly advantageous, however, are steviol glycosides which comply with the preceding composition and in which Very particularly advantageous, however, are steviol glycosides which comply with the preceding composition and in which
(a1) less than 5% by weight rebaudioside A,
(a2) less than 2% by weight rebaudioside B,
(a3) less than 5% by weight rebaudioside C,
(a4) less than 0.5% rebaudioside D, and
(a5) less than 5% by weight stevioside
are present.

These steviol glycoside compositions may be obtained by the further abovedescribed enzymatic or fermentative methods of WO 2012 112180 A1, WO 2012 128775 A1, WO 2012 129451 A1 and also WO 2013 096420 A1 from one or more of the following steviosides: rebaudioside A, rebaudioside B, rebaudioside C, rebaudioside D, rebaudioside E, rebaudioside F, stevioside, steviolbioside, rubusoside, dulcoside A. Where these documents describe the production of the steviol glycoside mixtures, the content thereof is hereby incorporated by reference.

The said substances rebaudioside A, rebaudioside B, rebaudioside C, rebaudioside D, rebaudioside E, rebaudioside F, stevioside, steviolbioside, rubusoside, dulcoside A may be produced in a manner known per se by extracting the leaves of *Stevia rebaudiana* or *Rubus suavissimus* with aqueous ethanol, wherein the extracts generally contain—without purification—about 1% by weight glycosides.

Starch Degradation Products

The starch degradation products which form the component ( ), in the mixtures have the function of carrier substances. Preferably, these are dextrins or maltodextrins which on the basis of their molecular size are between oligosaccharides and starch. Usually, they occur in the form of white or light-yellow power. They are principally recovered from wheat, potato and maize starch by dry heating (>150° C.) or under action of acid. In nature, dextrin, for example, is generated by *Bacterium macerans*. Dextrins are also formed by the enzymatic breakdown of starch by amylase.

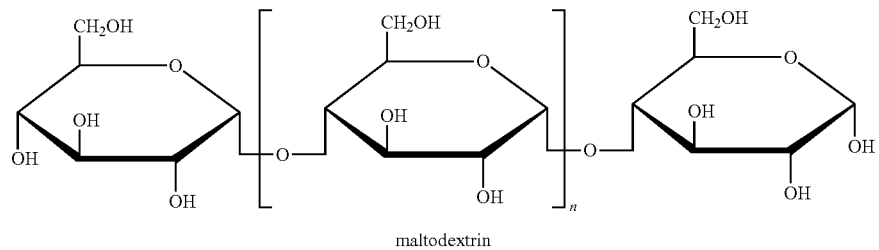

maltodextrin (a1) between 1 and 5% by weight rebaudioside A and rebaudioside A isomers, wherein one or more of the rebaudioside A isomers are present in relation to rebaudioside A at 5:1 to 1:5,
(a2) between 0.1 and 1% by weight rebaudioside B and rebaudioside B isomers,
(a3) between 1 and 5% by weight rebaudioside C and rebaudioside C isomers,
(a4) between 2 and 10% by weight rebaudioside D and rebaudioside D isomers, wherein one or more of the rebaudioside D isomers are present in relation to rebaudioside D at greater than 1:100 to 1:500,
(a5) less than 5% by weight stevioside and stevioside isomers, and
(a6) less than 5% by weight steviolbioside and steviolbioside isomers
are present.

Maltodextrins that are particularly suitable have about 3 to about 20, preferably about 5 to about 15, dextrose equivalents (DE). This is taken to mean the percentage fraction of the reducing sugars in the dry matter.

The components (a) and (b) are present in the mixtures of matter usually in the weight ratio of about 60:40 to about 90:10 and preferably about 70:30 to 80:20.

Phenolic Sweetness-Enhancing Aroma Substances

Phenolic sweetness-enhancing aroma substances which form the group (c) are characterized in that they are derived from the group of flavonoid derivatives, in particular flavanones, dihydrochalcones and neoisoflavanones with the proviso that at least one p-hydroxyphenyl or one 4-hydroxy-3-methoxyphenyl or one 4-methoxy-3-hydroxyphenyl group is present and are preferably selected from phloretin, 1-(2, 4-dihydroxyphenyl)-3-(3-hydroxy-4-methoxyphenyl)propan-1-one, 7,3-dihydroxy-4'-methoxyflavan and 5-hydroxy-4-(4-hydroxy-3-methoxyphenyl)-7-methoxy-2-chromanone and more preferably hesperetin.

Hesperetin is the aglycone of hesperidin and belongs to the flavanone group:

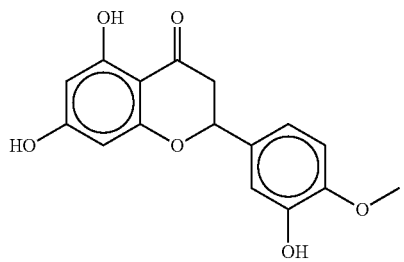

racemic hesperetin

Hesperetin can be used both as (S)- and (R)-form and also in any desired mixture of the two forms and in the form of physiologically compatible salts; in this case, reference is made to international patent application WO 2007 014,879 A1.

Phloretin is the aglycone of phloridizine and belongs to the dihydrochalcone group:

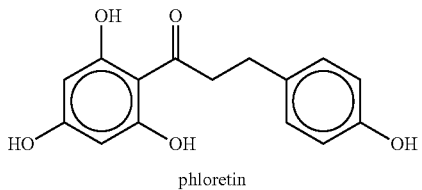

phloretin

Here, with respect to the preparation, reference is made to European patent application EP 1,998,636 A1.

Likewise, 1-(2,4-dihydroxyphenyl)-3-(3-hydroxy-4-methoxyphenyl)propan-1-one belongs to the dihydrochalcone group:

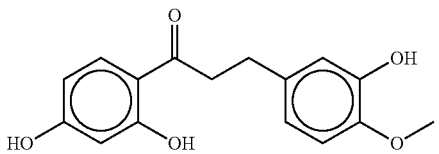

Here, reference is made with respect to the preparation to European patent application EP 2,353,403 A1.

7,3-Dihydroxy-4'-methoxyflavane belongs to the flavane group:

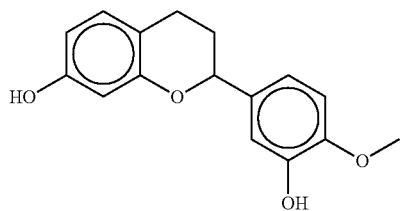

Here, reference is made with respect to the preparation to European patent application EP 2,253,226 A1.

The neoisoflavonoid 5-hydroxy-4-(4-hydroxy-3-methoxyphenyl)-7-methoxy-2-chromanone is given in the following picture and was disclosed in European patent application EP 2,570,036 A1:

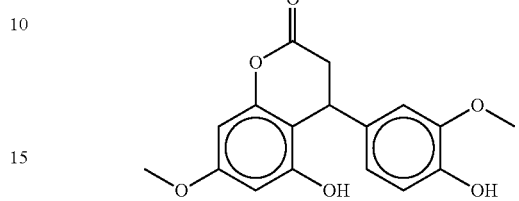

Mixtures of Matter

Preferably, the mixtures of matter according to the invention are distinguished in that they contain the components (a+b) and (c) in the weight ratio 1:99 to 99:1, preferably about 5:95 to about 75:25, particularly preferably about 25:75 to 75:25 and very particularly preferably about 5:95 to 25:75. A typical composition of the mixtures therefore appears as follows, for example:
(a) about 1 to about 99% by weight, preferably 5 to 50% by weight, steviol glycosides, particularly preferably
(b) about 0.1 to about 15% by weight, preferably about 0.5 to about 10% by weight, maltodextrins and
(c) about 0.1 to about 20% by weight, preferably about 0.5 to 10% by weight, of one or more of the phenolic sweetness-enhancing aroma substances
with the proviso that the indications of quantity total 100% by weight.

Oral Preparations

The present invention further relates to preparations for oral consumption which contain the mixtures according to the invention of the components (a), (b) and (c) preferably in amounts of 0.00001 to about 2% by weight. Further preferred amounts of ingredients are 0.0001 to about 1.5% by weight, in particular 0.001 to about 1% by weight, further preferably about 0.01 to about 0.5% by weight, and very particularly preferably about 0.05 to 0.1% by weight.

Food

In a first embodiment, the oral preparations can be selected from the group which is formed by
  bakery products, for example bread, dry biscuits, cakes, other baked goods,
  confectionary products (for example chocolates, chocolate bar products, other bar products, fruit gums, hard and soft caramels, chewing gum),
  alcoholic or non-alcoholic drinks (for example coffee, tea, iced tea, wine, wine-containing drinks, beer, beer-containing drinks, liquors, schnapps, brandies, (carbonated) fruit-containing lemonades, (carbonated) isotonic drinks, (carbonated) soft drinks, nectars, spritzers, fruit and vegetable juices,
  fruit or vegetable juice preparations,
  instant drinks (for example instant cocoa drinks, instant tea drinks, instant coffee drinks, instant fruit drinks),
  meat products (for example hams, fresh sausage or uncooked sausage preparations, seasoned or marinated fresh or picked meat products),
  eggs or egg products (dried egg, egg white, egg yolk),
  cereal products (for example breakfast cereals, muesli bars, prefermented ready-to-serve rice products), milk products (for example milk drinks, buttermilk drinks, dairy ice cream, yoghurt, kefir, fresh cheese, soft cheese, hard cheese, dried milk powder, whey, whey drinks, butter, buttermilk, products containing partially or fully hydrolyzed milk protein), products of soya protein or other soya bean fractions (for example soya milk and products made therefrom, fruit drinks containing soya protein, soy lecithin-containing preparations, fermented products such as tofu or tempeh or products made therefrom), products of other plant protein sources, for example oat protein drinks, fruit preparations (for example jams, fruit ice cream, fruit sauces, fruit fillings), vegetable preparations (for example ketchup, sauces, dried vegetables, frozen vegetables, precooked vegetables, bottled vegetables), snack articles (for example baked or fried potato crisps or potato dough products, maize or peanut-based extrudates), fat- and oil-based products or emulsions of the same (for example mayonnaise, remoulade, dressings), other ready-to-serve meals and soups (for example dried soups, instant soups, precooked soups), spices, spice mixtures and also in particular seasonings which are used, for example, in the snack sector.

Particular preference is given here to confectionary products, milk products, and very particularly non-alcoholic drinks, wherein sweetened drinks are preferred.

Auxiliaries and Additives

These foods can typically contain further auxiliaries and additives, including, in particular, sweeteners, food acids, acidity regulators, thickeners, and in particular further aroma substances.

Sweeteners

As sweeteners, or sweet-tasting additives, firstly carbohydrates and especially sugars come into consideration, such as, for instance sucrose/saccharose, trehalose, lactose, maltose, melizitose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, or maltodextrin. Equally suitable are plant preparations which contain these substances, for example based on sugar beets (*Beta vulgaris* ssp., sugar fractions, sugar syrup, melasse), sugarcane (*Saccharum officinarum* ssp., melasse, sugarcane syrup), maple syrup (*Acer* ssp.) or agave (agave thick juice).

Those which also come into consideration are synthetic, i.e. generally enzymatically produced starch or sugar hydrolysates (invert sugar, fructose syrup);

fruit concentrates (e.g. based on apples or pears);

sugar alcohols (e.g. erythritol, threitol, arabitol, ribotol, xylitol, sorbitol, mannitol, dulcitol, lactitol);

proteins (e.g. miraculin, monellin, thaumatin, curculin, brazzein);

sweeteners (e.g. MAGAP, sodium cyclamate, acesulfame K, neohesperidin dihydrochalcone, saccharin sodium salt, aspartame, superaspartame, neotame, alitame, sucralose, steviosides, rebaudiosides, lugduname, carrelame, sucrononates, sucrooctates, monatin, phenylodulcin);

sweet-tasting amino acids (e.g. glycine, D-leucine, D-threonine, D-asparagine, D-phenylalanine, D-tryptophan, L-proline);

further sweet-tasting low-molecular-weight substances such as, e.g., hernandulcin, dihydrochalcone glycosides, in particular neohesperidin dihydrochalcone and naringin chalcone, glycyrrhizin, glycyrrhetic acid, derivatives and salts thereof, extracts of liquorice (*Glycyrrhizza glabra* ssp.), *Lippia dulcis* extracts, *Momordica* ssp. extracts or individual substances such as, e.g., *Momordica grosvenori* [Luo Han Guo] and the mogrosides obtained therefrom, *Hydrangea dulcis* or extracts or phyllodulcin.

Balansins from *Mycetia balansae*.

Food Acids

The foods can contain carboxylic acids. Acids in the context of the invention are preferably acids permitted in foods, in particular those mentioned here:

E 260—acetic acid
E 270—lactic acid
E 290—carbon dioxide
E 296—malic acid
E 297—fumaric acid
E 330—citric acid
E 331—sodium citrate
E 332—potassium citrate
E 333—calcium citrate
E 334—tartaric acid
E 335—sodium tartrate
E 336—potassium tartrate
E 337—sodium-potassium tartrate
E 338—phosphoric acid
E 353—metatartaric acid
E 354—calcium tartrate
E 355—adipic acid
E 363—succinic acid
E 380—triammonium citrate
E 513—sulphuric acid
E 574—gluconic acid
E 575—glucono-delta-lactone Acidity Regulators Acidity regulators are food additives which keep constant the acidity or basicity and thereby the desired pH of a food. They are mostly organic acids and salts thereof, carbonates, and more rarely also inorganic acids and salts thereof. The addition of an acidity regulator partly increases the stability and firmness of the food, effects a desired precipitation and improves the action of preservatives. In contrast to acidulants, they are not used for taste modification of foods. Their action is based on the formation of a buffer system in the food in which the pH is not changed or is changed only slightly on addition of acidic or basic substances. Examples are:

E 170—calcium carbonate
E 260-263—acetic acid and acetates
E 270—lactic acid
E 296—malic acid
E 297—fumaric acid
E 325-327—lactates (lactic acid)
E 330-333—citric acid and citrates
E 334-337—tartaric acid and tartrates
E 339-341—orthophosphates
E 350-352—malates (malic acid)
E 450-452—di-, tri- and polyphosphates
E 500-504—carbonates (carbon dioxide)
E 507—hydrochloric acid and chlorides
E 513-517—sulphur acid and sulphates
E 524-528—hydroxides
E 529-530—oxides
E 355-357—adipic acid and adipates
E 574-578—gluconic acid and gluconates Thickeners Thickeners are substances which are primarily able to bind water. By withdrawal of unbound water, the viscosity increases. From a concentration which is characteristic for each thickener, in addition to this effect, network effects also occur which lead to a usually disproportional increase in viscosity. In this case molecules are said to "communicate" with one another, i.e. become entangled. Most thickeners are linear or branched macromolecules (e.g. polysaccharides or proteins) which can interact with one another via intermolecular interactions, such as hydrogen bridges, hydrophobic interactions or ionic relationships. Extreme cases of thickeners are sheet silicates (bentonites, hectorites) or hydrated $SiO_2$ particles which are present in dispersed form as particles and can bind water in their solid-like structure or, on account of the described interactions, can interact with one another. Examples are:

E 400—alginic acid
E 401—sodium alginate
E 402—potassium alginate
E 403—ammonium alginate
E 404—calcium alginate
E 405—propylene glycol alginate
E 406—agar agar
E 407—carrageenan, furcelleran
E 407—carob bean meal
E 412—guar kernel meal
E 413—tragacanth
E 414—gum arabic
E 415—xanthan
E 416—karaya (Indian tragacanth)
E 417—tara gum meal (Peruvian carob bean meal)
E 418—gellan
E 440—pectin, Opekta
E 440ii—amidated pectin
E 460—microcrystalline cellulose, cellulose powder
E 461—methylcellulose
E 462—ethylcellulose
E 463—hydroxypropyl cellulose
E 465—methylethyl cellulose
E 466—carboxymethyl cellulose, sodium carboxymethyl cellulose Aroma Substances The oral preparations according to the invention can contain one or more aroma substances. Typical examples comprise: acetophenone, allyl caproate, alpha-ionone, beta-ionone, anisaldehyde, anisyl acetate, anisyl formate, benzaldehyde, benzothiazole, benzyl acetate, benzyl alcohol, benzyl benzoate, beta-ionone, butyl butyrate, butyl caproate, butylidene phthalide, carvone, camphene, caryophyllene, cineole, cinnamyl acetate, citral, citronellol, citronellal, citronellyl acetate, cyclohexyl acetate, cymene, damascone, decalactone, dihydrocoumarin, dimethyl anthranilate, dodecalactone, ethoxyethyl acetate, ethylbutyric acid, ethyl butyrate, ethyl caprate, ethyl caproate, ethyl crotonate, ethylfuraneol, ethylguaiacol, ethyl isobutyrate, ethyl isovalerate, ethyl lactate, ethyl methylbutyrate, ethyl propionate, eucalyptol, eugenol, ethyl heptylate, 4-(p-hydroxyphenyl)-2-butanone, gamma-decalactone, geraniol, geranyl acetate, grapefruit aldehyde, methyl dihydrojasmonate (e.g. Hedion), heliotropin, 2-heptanone, 3-heptanone, 4-heptanone, trans-2-heptenal, cis-4-heptenal, trans-2-hexenal, cis-3-hexenol, trans-2-hexenic acid, trans-3-hexenic acid, cis-2-hexenyl acetate, cis-3-hexenyl acetate, cis-3-hexenyl caproate, trans-2-hexenyl caproate, cis-3-hexenyl formate, cis-2-hexyl acetate, cis-3-hexyl acetate, trans-2-hexyl acetate, cis-3-hexyl formate, para-hydroxybenzylacetone, isoamyl alcohol, isoamylisovalerate, isobutyl butyrate, isobutyraldehyde, isoeugenol methyl ether, isopropyl methylthiazole, lauric acid, laevulinic acid, linalool, linalool oxide, linalyl acetate, menthol, menthofuran, methyl anthranilate, methylbutanol, methylbutyric acid, 2-methylbutyl acetate, methyl caproate, methyl cinnamate, 5-methylfurfural, 3,2,2-methylcyclopentenolone, 6,5,2-methylheptenone, methyl dihydrojasmonate, methyl jasmonate, 2-methylmethylbutyrate, 2-methyl-2-pentenolic acid, methyl thiobutyrate, 3,1-methylthiohexanol, 3-methylthiohexyl acetate, nerol, neryl acetate, trans,trans-2,4-nonadienal, 2,4-nonadienol, 2,6-nonadienol, noot-katone, delta-octalactone, gamma-octalactone, 2-octanol, 3-octanol, 1,3-octenol, 1-octyl acetate, 3-octyl acetate, palmitic acid, paraldehyde, phellandrene, pentanedione, phenylethyl acetate, phenylethyl alcohol, phenylethyl isovalerate, piperonal, propionaldehyde, propyl butyrate, pulegone, pulegol, sinensal, sulfurol, terpinene, terpineol, terpinolene, 8,3-thiomenthanone, 4,4,2-thiomethylpentanone, thymol, delta-undecalactone, gamma-undecalactone, valencene, valeric acid, vanillin, acetoin, ethylvanillin, ethylvanillin isobutyrate (=3-ethoxy-4-isobutyryloxybenzaldehyde), 2,5-dimethyl-4-hydroxy-3(2H)-furanone and derivatives thereof (here preferably homofuraneol (=2-ethyl-4-hydroxy-5-methyl-3(2H)-furanone), homofuronol (=2-ethyl-5-methyl-4-hydroxy-3(2H)-furanone and 5-ethyl-2-methyl-4-hydroxy-3(2H)-furanone), maltol and maltol derivatives (here preferably ethylmaltol), coumarin and coumarin derivatives, gamma-lactones (here preferably gamma-undecalactone, gamma-nonalactone, gamma-decalactone), delta-lactones (here preferably 4-methyldeltadecalactone massoilactone, delta-decalactone, tuberolactone), methyl sorbate, divanillin, 4-hydroxy-2(or 5)-ethyl-5(or 2)-methyl-3(2H)furanone, 2-hydroxy-3-methyl-2-cyclopentenone, 3-hydroxy-4,5-dimethyl-2(5H)-furanone, isoamyl acetate, ethyl butyrate, n-butyl butyrate, isoamyl butyrate, ethyl 3-methylbutyrate, ethyl n-hexanoate, allyl n-hexanoate, n-butyl n-hexanoate, ethyl n-octanoate, ethyl-3-methyl-3-phenylglycidate, ethyl 2-trans-4-cis-decadienoate, 4-(p-hydroxyphenyl)-2-butanone, 1,1-dimethoxy-2,2,5-trimethyl-4-hexane, 2,6-dimethyl-5-hepten-1-al and phenylacetaldehyde, 2-methyl-3-(methylthio)furan, 2-methyl-3-furanthiol, bis(2-methyl-3-furyl)disulphide, furfuryl mercaptan, methional, 2-acetyl-2-thiazoline, 3-mercapto-2-pentanone, 2,5-dimethyl-3-furanthiol, 2,4,5-trimethylthiazole, 2-acetylthiazole, 2,4-dimethyl-5-ethylthiazole, 2-acetyl-1-pyrroline, 2-methyl-3-ethylpyrazine, 2-ethyl-3,5-dimethyl pyrazine, 2-ethyl-3,6-dimethylpyrazine, 2,3-diethyl-5-methylpyrazine, 3-isopropyl-2-methoxypyrazine, 3-isobutyl-2-methoxypyrazine, 2-acetylpyrazine, 2-pentylpyridine, (E,E)-2,4-decadienal, (E,E)-2,4-nonadienal, (E)-2-octenal, (E)-2-nonenal, 2-undecenal, 12-methyltridecanal, 1-penten-3-one, 4-hydroxy-2,5-dimethyl-3(2H)-furanone, guaiacol, 3-hydroxy-4,5-dimethyl-2(5H)-furanone, 3-hydroxy-4-methyl-5-ethyl-2(5H)-furanone, cinnamaldehyde, cinnamyl alcohol, methyl salicylate, isopulegol and also (not explicitly stated here) stereoisomers, enantiomers, positional isomers, diastereomers, cis/trans isomers or epimers of these substances.

Oral and Dental Care Compositions

In a further embodiment, the oral preparations can be selected from the group that is formed by oral and dental care compositions which also include mouthwashes and chewing gums.

Specific examples thereof are toothpastes, tooth gels, tooth powders, mouthwashes and the like. Toothpastes or tooth creams are generally taken to mean gel-type or pasty preparations of water, thickeners, moisture-retention agents, abrasive or cleaning bodies, surfactants, sweeteners, aroma substances, deodorizing active ingredients and also active ingredients against oral and dental diseases. All customary cleaning bodies, such as, e.g. chalk, dicalcium phosphate, insoluble sodium metaphosphate, aluminium silicates, calcium pyrophosphate, finely divided synthetic resins, silicas, aluminium oxide and aluminium oxide trihydrate can be used in the toothpastes according to the invention.

Preferably suitable cleaning bodies for the toothpastes according to the invention are, especially, finely divided xerogel silicas, hydrogel silicas, precipitated silicas, aluminium oxide trihydrate and finely divided alpha-aluminium oxide or mixtures of these cleaning bodies in amounts of 15 to 40% by weight of the toothpaste. As moisture-retention agents, principally low-molecular-weight polyethylene glycols, glycerol, sorbitol or mixtures of these products in amounts up to 50% by weight come into consideration. Among the known thickeners, the thickening, finely divided gel silicas and hydrocolloids, such as, e.g. carboxymethylcellulose, hydroxyethylcellulose, hydroxypropyl guar, hydroxyethyl starch, polyvinylpyrrolidone, high-molecular-weight polyethylene glycol, plant gums such as tragacanth, agar-agar, carrageen moss, gum arabic, xantham gum and carboxyvinylpolymers (e.g. Carbopol® types) are suitable. In addition to the mixtures of menthofuran and menthol compounds, the oral and dental care compositions can in particular surface-active substances, preferably anionic and nonionic high-foam surfactants, such as the abovementioned substances, but in particular alkylether sulphate salts, alkyl polyglucosides and mixtures thereof.

Further customary toothpaste additives are:
preservatives and antimicrobial substances such as, e.g. methyl, ethyl or propyl p-hydroxybenzoates, sodium sorbate, sodium benzoate, bromochlorophene, phenyl salicylate, thymol and the like;
antitartar active ingredients, e.g. organophosphates such as 1-hydroxyethane-1,1-diphosphonic acid, 1-phosphonpropane-1,2,3-tricarboxylic acid and others, which are known, e.g. from U.S. Pat. No. 3,488,419, DE 2224430 A1 and DE 2343196 A1;
other anticaries substances such as, e.g., sodium fluoride, sodium monofluorophosphate, tin fluoride;
sweetening agents, such as, e.g. saccharin sodium, sodium cyclamate, sucrose, lactose, maltose, fructose or Apartam®, (L-aspartyl L-phenylalanine methyl ester), stevia extracts or the sweetening components thereof, in particular rebeaudiosides;
additional flavourings such as, e.g. eucalyptus oil, aniseed oil, fennel oil, cumin oil, methyl acetate, cinnaldehyde, anethol, vanillin, thymol and also mixtures of these and other natural and synthetic flavourings;
pigments such as, e.g., titanium dioxide;
dyes;
buffer substances such as, e.g. primary, secondary or tertiary alkali metal phosphates or citric acid/sodium citrate;
wound-healing and anti-inflammatory substances such as, e.g. allantoin, urea, azulene, chamomile active ingredients and acetylsalicylic acid derivatives.

A preferred embodiment of the cosmetic preparations is toothpastes in the form of an aqueous, pasty dispersion, containing polishing agents, moisture-retention agents, viscosity regulators and optionally contain further customary components, and also the mixture of menthofuran and menthol compounds in amounts of 0.5 to 2% by weight.

In mouthwashes, a combination with aqueous-alcoholic solutions of various concentration gradients of essential oils, emulsifiers, astringent and toning drug extracts, tartar-inhibiting, antibacterial additives and flavour correctors is easily possible. A further preferred embodiment of the invention is a mouthwash in the form of an aqueous or aqueous-alcoholic solution containing the mixture of menthofuran and menthol compounds in amounts of 0.5 to 2% by weight. In mouthwashes which are diluted before application, adequate effects can be achieved with higher concentrations corresponding to the intended dilution ratio.

To improve the flow behaviour, in addition, hydrotropic agents, for example ethanol, isopropyl alcohol or polyols can be used; these substances correspond substantially to the carriers described at the outset. Polyols which come into consideration here preferably have 2 to 15 carbon atoms and at least two hydroxyl groups. The polyols can contain even further functional groups, in particular amino groups, or be modified by nitrogen. Typical examples are
glycerol;
alkylene glycols, such as, for example, ethylene glycol, diethylene glycol, propylene glycol, butylene glycol, hexylene glycol and also polyethylene glycols having an average molecular weight from 100 to 1,000 daltons;
technical oligoglycerol mixtures having a degree of self-condensation of 1.5 to 10 such as technical diglycerol mixtures having a diglycerol content of 40 to 50% by weight;
methylol compounds such as, in particular, trimethylol ethane, trimethylol propane, trimethylol butane, pentaerythritol and dipentaerythritol;
low-alkyl glucosides, in particular those having 1 to 8 carbon atoms in the alkyl radical, such as, for example, methyl and butyl glucoside;
sugar alcohols having 5 to 12 carbon atoms, such as, for example, sorbitol or mannitol,
sugars having 5 to 12 carbon atoms, such as, for example, glucose or sucrose;
amino sugars, such as, for example, glucamine;
dialcoholamines, such as diethanolamine or 2-amino-1,3-propanediol.

Suitable preservatives are, for example, phenoxyethanol, formaldehyde solution, parabens, pentanediol or sorbic acid, and also the silver complexes known under the name Surfacine® and the further classes of substances listed in annex 6, part A and B of the cosmetics regulation.

Perfume oils which may be mentioned are mixtures of natural and synthetic odour substances. Natural odour substances are extracts of blossoms (lily, lavender, roses, jasmine, neroli, ylang-ylang), stalks and leaves (geranium, patchouli, petitgrain), fruits (aniseed, coriander, cumin, juniper), fruit skins (bergamot, lemon, oranges), roots (mace, angelica, celeriac, cardamom, costus, iris, calmus), woods (pine, sandal, guaiac, cedar, rosewood), herbs and grasses (tarragon, lemon grass, sage, thyme), needles and twigs (spruce, fir, pine, mountain pine), resins and balsams (galbanum, elemi, benzoin, myrrh, olibanum, opoponax). In addition, animal raw materials come into consideration, such as, for example, civet and castoreum. Typical synthetic odour substance compounds are products of the type of esters, ethers, aldehydes, ketones, alcohols and hydrocarbons. Odour substance compounds of the ester type are, e.g. benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexylpropionate, styrallyl propionate and benzyl salicylate. The ethers include, for example, benzyl ethyl ether, the aldehydes include, e.g. the linear alkanals having 8 to 18 carbon atoms, citral, citronellal, citronellyloxyacetaldehyde, cyclamen aldehyde, hydroxycitronellal, lilial and bourgeonal, the ketones include, e.g., the ionones, α-isomethylionone and methyl cedryl ketone, the alcohols include anethole, citronellol, eugenol, isoeugenol, geraniol, linalool, phenylethyl alcohol and terpineol, the hydrocarbons include chiefly the terpenes and balsams. However, preference is given to using mixtures of various odour substances which together generate a corresponding fragrance note. Also essential oils of lower volatility which are generally used as aroma components are suitable as perfume oils, e.g. salvia oil, chamomile oil, clove oil, melissa oil, mint oil, cinnamon leaf oil, linden blossom oil, juniper berry oil, vetiver oil, olibanum oil, galbanum oil, labolanum oil and lavender oil. Preferably, bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, Ambroxan, indole, hedione, sandelice, lemon oil, mandarin oil, orange oil, allyl amyl glycolate, cyclovertal, lavender oil, Salvia sclarea oil, β-damascone, geranium bourbon oil, cyclohexyl salicylate, Vertofix Coeur, Iso-E-Super, Fixolide NP, evernyl, iraldein gamma, phenylacetic acid, geranyl acetate, benzyl acetate, rose oxide, romilllate, irotyl and floramate are used alone or in mixtures.

As flavourings, for example, peppermint oil, spearmint oil, aniseed oil, star anise oil, cumin oil, eucalyptus oil, fennel oil, lemon oil, wintergreen oil, clove oil, menthol and the like come into consideration.

Chewing Gums

Where the oral preparations are chewing gums, these typically contain a water-insoluble component and a water-soluble component.

"The water-insoluble base, also known as gum base", usually comprises natural or synthetic elastomers, resins, fats and oils, plasticizers, fillers, dyes and also optionally waxes. The fraction of base of the total composition is usually 5 to 95% by weight, preferably 10 to 50% by weight and in particular 20 to 35% by weight. In a typical embodiment of the invention, the base is 20 to 60% by weight composed of synthetic elastomers, 0 to 30% by weight natural elastomers, 5 to 55% by weight plasticizers, 4 to 35% by weight fillers and in subsidiary amounts additives such as dyes, antioxidants and the like, with the proviso that they are water-soluble, at all events in small amounts.

Suitable synthetic elastomers are, for example, polyisobutylenes having average molecular weights (according to GPC) of 10,000 to 100,000, and preferably 50,000 to 80,000, isobutylene-isoprene-copolymers ("butyl elastomers"), styrene-butadiene-copolymers (styrene:butadiene ratio e.g. 1:3 to 3:1), polyvinylacetates having average molecular weights (according to GPC) of 2000 to 90,000, and preferably 10,000 to 65,000, polyisoprenes, polyethylene, vinyl acetate-vinyl laurate copolymers and mixtures thereof. Examples of suitable natural elastomers are rubbers, for instance smoked or liquid latex or Guayule and also natural rubbers such as jelutong, lechi caspi, perillo, sorva, massaranduba balata, massaranduba chocolate, nispero, rosindinba, chicle, gutta hang kang, and also mixtures thereof. The selection of synthetic and natural elastomers and mixing ratios thereof is directed substantially according to whether bubbles are to be generated ("bubble gums") or not with the chewing gums. Preferably, elastomer mixtures are used which contain jelutong, chicle, sorva and massaranduba.

In most cases, the elastomers prove in processing to be too hard or insufficiently manageable, and so it has proved advantageous to use conjointly specific plasticizers which of course must in particular also meet all the requirements to be permitted as food additives. In this respect, chiefly esters of resin acids come into consideration, for example esters of low aliphatic alcohols or polyols with completely or partially hardened, monomeric or oligomeric resin acids. In particular for this purpose, the methyl, glycerol or pentarerythrityl esters and also mixtures thereof are used. Alternatively, terpene resins also come into consideration which can be derived from alpha-pinene, beta-pinene, delta-limonene or mixtures thereof.

As fillers or texturizing agents come magnesium or calcium carbonate, ground pumice stone, silicates, especially magnesium or aluminium silicates, clays, aluminas. Talcum, titanium dioxide, mono-, di- and tricalciumphosphate and also cellulose polymers.

Suitable emulsifiers are tallow, hardened tallow, hardened or partially hardened vegetable oils, cocoa butter, partial glycerides, lecithin, triacetin and saturated or unsaturated fatty acids having 6 to 22, and preferably 12 to 18, carbon atoms, and also mixtures thereof.

As dyes and whitening agents, for example the FD and C types, plant and fruit extracts and also titanium dioxide permitted for colouring foods come into consideration.

The base compositions can contain waxes or be wax free; examples of wax-free compositions may be found, inter alia, in the patent document U.S. Pat. No. 5,286,500, the content of which is hereby explicitly incorporated by reference.

In addition to the water-insoluble gum base, chewing gum preparations regularly contain a water-soluble fraction which is formed, for example, by softeners, sweeteners, fillers, taste substances, taste intensifiers, emulsifiers, dyes, acidulants, antioxidants and the like, here with the proviso that the components have an at least adequate water solubility. Depending on the water solubility of the specific representatives, therefore, individual components can either belong to the water-insoluble phase or else the water-soluble phase. However, it is also possible to use combinations, for example of a water-soluble emulsifier and a water-insoluble emulsifier, wherein the individual representatives are then situated in different phases. Usually, the water-insoluble fraction makes up 5 to 95% by weight, and preferably 20 to 80% by weight, of the preparation.

Water-soluble softeners or plasticizing agents are added to the chewing gum compositions in order to improve the chewability and the chewing feel and are present in the mixtures typically in amounts of 0.5 to 15% by weight. Typical examples are glycerol, lecithin and also aqueous solutions of sorbitol, hardened starch hydrolysates or corn syrup.

As sweeteners, both sugar-containing and sugar-free compounds come into consideration which are used in amounts of 5 to 95% by weight, preferably 20 to 80% by weight, and in particular 30 to 60% by weight, based on the chewing gum composition. Typical saccharide sweeteners are sucrose, dextrose, maltose, dextrin, dried invert sugar, fructose, levulose, galactose, corn syrup, and also mixtures thereof. As sugar replacers, sorbitol, mannitol, xylitol, hardened starch hydrolysates, maltitol and mixtures thereof come into consideration. In addition, as additives, what are termed High Intensity Artificial Sweeteners (HIAS) also come into consideration, such as, for example, sucralose, aspartame acesulfame salts, alitame, saccharin and saccharin salts, cyclamic acid and salts thereof, glycyrrhizins, dihydrochalcones, thaumatin, monellin and the like, alone or in mixtures.

In particular, for the production of low-calorie chewing gums, fillers such as, for example, polydextrose, raftilose, Rafitilin, fructooligosaccharides (NutraFlora), palatinose oligosaccharides, guar gum hydrolysates (Sun Fiber) and also dextrins are suitable.

The selection of further taste substances is virtually unlimited and is non-critical for the essence of the invention. Usually, the total fraction of all taste substances is 0.1 to 15% by weight, and preferably 0.2 to 5% by weight, based on the chewing gum composition. Suitable further taste substances are, for example, essential oils, synthetic flavourings and the like, such as, for instance, aniseed oil, star anise oil, cumin oil, eucalyptus oil, fennel oil, lemon oil, wintergreen oil, clove oil and the like, as are also used, for example, in oral and dental care compositions.

The chewing gums can in addition contain further auxiliaries and additives which are suitable, for example, for tooth care, especially for combating plaque and gingivitis, such as, e.g., chlorhexidine, CPC or triclosan. In addition, pH regulators (e.g. buffers or urea), substances active against caries (e.g. phosphates or fluorides), biogenic active ingredients (antibodies, enzymes, caffeine, plant extracts) may be present, provided that these substances are permitted for foods, and do not interact with one another in an undesired manner.

INDUSTRIAL APPLICABILITY

The present invention further relates to firstly, a method for taste optimization of preparations directed towards oral consumption, which is distinguished in that about 0.0001 to about 2% by weight of the mixtures containing the components (a), (b) and (c) are added to said preparations.

The present invention equally relates to a method for solubility enhancement of aroma substances in preparations for oral consumption, which is characterized in that said preparations are used together with 0.0001 to 2% by weight of the mixtures containing the components (a), (b) and (c).

Finally, the invention relates on the one hand to the use of the mixtures containing the components (a), (b) and (c), firstly as aroma substances for preparations for oral consumption, and also secondly as solubility enhancers for other aroma substances.

With respect to the preferred compositions of the mixtures, the preferred usage or addition rates, and also the nature of the aroma substances, reference is made to that stated hereinbefore.

EXAMPLES

Examples 1 and 2

TABLE 1

Composition of the steviol glycoside mixtures containing starch breakdown products

| Ingredients | A | B | C | D | E |
|---|---|---|---|---|---|
| Starch breakdown products (maltodextrins) | 3.4 | 4.8 | 4.9 | 15.0 | 15.0 |
| Rebaudioside A | 0.9 | 1.0 | 0.8 | 3.6 | 1.4 |
| Rebaudioside B | 1.3 | 1.0 | 0.5 | 0.51 | 0.48 |
| Rebaudioside C | 2.6 | 2.0 | 1.0 | 0.91 | 1.2 |
| Rebaudioside D | 0.1 | 0.2 | 0.2 | 0.082 | 0.082 |
| Stevioside | 3.0 | 3.1 | 3.7 | 1.5 | 3.2 |
| Steviolbioside | 1.2 | 1.6 | 2.0 | 0.13 | 0.64 |
| Steviol glycosides (3-fold, stevioside isomers, dulcoside A isomers, rebaudioside B isomers) | 11.6 | 9.8 | 12.1 | 10.0 | 10.0 |
| Steviol glycosides (4-fold, rebaudioside A isomers, rebaudioside C isomers, rebaudioside E isomers, rebaudioside F isomers) | 10.5 | 10.4 | 7.1 | 2.6 | 5.3 |
| Steviol glycosides (5-fold, rebaudioside D isomers) | 8.7 | 8.5 | 8.4 | 5.72 | 4.44 |
| Steviol glycosides (6-fold) | 10.3 | 9.8 | 8.4 | 8 | 8 |
| Steviol glycosides (7-fold) | 10.7 | 10.3 | 12.6 | 13 | 13 |
| Steviol glycosides (8-fold) | 6.2 | 6.9 | 6.8 | 7.0 | 7.0 |
| Steviol glycosides (9-fold) | 7.0 | 6.3 | 7.2 | 7.0 | 7.0 |
| Steviol glycosides (10-fold) | 4.3 | 4.8 | 4.8 | 5.0 | 5.0 |
| Steviol glycosides (11-fold) | 2.7 | 3.9 | 4.6 | 4.0 | 4.0 |
| Steviol glycosides (12-fold) | 2.7 | 2.5 | 2.1 | 2.0 | 2.0 |
| Steviol glycosides (13-fold) | 1.1 | 1.3 | 0.4 | 0.5 | 0.5 |
| Steviol glycosides (14-fold) | 0.6 | 0.4 | 0.6 | 1 | 1 |
| Steviol glycosides (15-fold) | 0.6 | 0.4 | 0.6 | 0.4 | 0.4 |
| Steviol glycosides (16+-fold) | 2.0 | 2.3 | 2.1 | 2.1 | 2.1 |
| Water (Karl-Fischer) | 7.3 | 6.1 | 5.2 | 5 | 6 |
| TOTAL | 98.7 | 97.5 | 96.0 | 95.1 | 97.7 |

TABLE 2

Composition of steviol glycoside mixtures

| Ingredients | A | B | C | D | E | F | G | H | I | J | K |
|---|---|---|---|---|---|---|---|---|---|---|---|
| Steviol biglucosides (e.g. steviolbioside, rubusoside) | 1.1 | 0.6 | 1.3 | 0.6 | 1 | 2.4 | 7.2 | 6.7 | 1.3 | 10.6 | 0.8 |
| Steviol triglucosides (e.g. stevioside, rebaudioside B and isomers) | 2.9 | 7.7 | 7.5 | 3.4 | 2.4 | 5.7 | 9.3 | 8.7 | 12 | 5.7 | 1.6 |
| Steviol tetraglucosides (e.g. Reb A, C and isomers) | 10.3 | 12.7 | 13.1 | 9.7 | 8.5 | 6.6 | 19.8 | 20.8 | 24.3 | 13.6 | 8.3 |
| Steviol pentaglucosides (e.g. Reb D and isomers) | 13.3 | 19.2 | 20.3 | 10.4 | 7.5 | 9 | 16.5 | 16.3 | 26 | 15.5 | 10.7 |
| Steviol hexaglucosides | 20.2 | 10.4 | 10.8 | 12.6 | 14 | 12.9 | 18.9 | 20.6 | 4.7 | 16.7 | 9 |
| Steviol heptaglucosides | 14.4 | 9.7 | 8 | 10.6 | 10.7 | 12.1 | 11.8 | 11.4 | 6.8 | 13.6 | 13 |
| Steviol octaglucosides | 12 | 9.5 | 8.9 | 10.6 | 9.5 | 10.8 | 6.2 | 7.4 | 9.7 | 7.9 | 11.5 |
| Steviol nonaglucosides | 9.9 | 6.9 | 8.7 | 9.6 | 9 | 8.6 | 3.9 | 2.3 | 4.2 | 6.5 | 11.8 |
| Steviol decaglucosides | 6.1 | 6.4 | 5.1 | 6.9 | 11.4 | 6.8 | 1.5 | 1.8 | 2.8 | 4.7 | 6.7 |
| Steviol undecaglucosides | 3.1 | 4.5 | 4.3 | 6.5 | 8.4 | 7 | 1.4 | 0.5 | 1.5 | 1.5 | 9.7 |
| Steviol dodecaglucosides | 1.8 | 5.3 | 4.8 | 2.8 | 4.1 | 4.6 | 0.3 | 0.3 | 1.2 | 0.3 | 4.1 |
| Steviol tridecaglucosides | 0.5 | 2.1 | 2 | 5.4 | 5.4 | 5.5 | 0.2 | 0.2 | 2.8 | 0.3 | 4.5 |
| Steviol tetradecaglucosides | 0.4 | 0.3 | 0.6 | 2.8 | 1.4 | 1.2 | 0.2 | 0.2 | 0.9 | 0.3 | 3.4 |

TABLE 2-continued

Composition of steviol glycoside mixtures

| Ingredients | A | B | C | D | E | F | G | H | I | J | K |
|---|---|---|---|---|---|---|---|---|---|---|---|
| Steviol pentadecaglucosides | 0.3 | 0.3 | 0.3 | 2.3 | 1.8 | 0.5 | 0.2 | 0.2 | 0.1 | 0.2 | 1.5 |
| Steviol-16-22-glucosides | 1.3 | 1.5 | 1.4 | 2.5 | 1.7 | 2.1 | 0.7 | 0.7 | 0.6 | 0.9 | 1.1 |
| Steviol-22-28-glucosides | 0.6 | 0.7 | 0.6 | 0.6 | 0.8 | 0.9 | 0.4 | 0.4 | 0.4 | 0.4 | 0.4 |
| Steviol-28-60-glucosides | 1.1 | 1.3 | 1.3 | 1.5 | 1.4 | 2 | 1 | 1 | 0.5 | 0.8 | 0.9 |
| Total steviosides | 99.3 | 99.1 | 99.0 | 98.9 | 99.0 | 98.7 | 99.5 | 99.5 | 99.8 | 99.5 | 99.0 |

TABLE 3

Aroma preparations

| Composition | A | B | C | D | E | F | G | H | I | J |
|---|---|---|---|---|---|---|---|---|---|---|
| Steviol glycoside mixture A containing maltodextrins from Example 1a | 10 | 20 | 10 | | | 10 | | 10 | | |
| Steviol glycoside mixture E containing maltodextrins from Example 1a | | | | 20 | 15 | | 7.5 | | | |
| Steviol glycoside mixture F Example 1b | | | | | | | | | 20 | |
| Steviol glycoside mixture I Example 1b | | | | | | | | | | 20 |
| Hesperetin from citrus (racemic, >80%) | 2 | | | | | | 2 | | | |
| (S)-Hesperetin from honey bush (>95%) | | | 1 | | | 1.5 | | | | |
| Phloretin | | | 2 | | | 2 | | | | |
| Hesperetin | | 3 | | 3 | 1 | | | 2 | | 3 |
| 1-(2,4-Dihydroxyphenyl)-3-(3-hydroxy-4-methoxyphenyl)-propan-1-one | | | | | | 2 | | | | |
| 7,3-Dihydroxy-4'-methoxyflavan | | | | | 2 | | | | | |
| 5-Hydroxy-4-(4-hydroxy-3-methoxyphenyl)-7-methoxy-2-chromanone | | | | | | 2 | | | | |
| Glycerol | 10 | 20 | | 30 | | 20 | 15 | 30 | 10 | 20 |
| Gum arabic solution (20%) | | | | | | | 10 | | | |
| 1,2-Propylene glycol | Ad 100 | | | | | | | | | |

Example 3

Drink Formulation

Various mixtures of matter based on steviol glycosides were used for producing simple soft drinks and the products were stored for 48 h at 20° C. Subsequently, the taste properties (descriptors: initial sweetness, sweetness intensity, sugar taste/fullness in the mouth) were assessed by a panel consisting of 8 trained testers on a linear scale of 0 (not present) to 10 (highly expressed). The compositions and results are summarized in Table 4 hereinafter. Embodiments 1 to 2 are according to the invention, and Examples V1 to V3 serve for comparison. Example C corresponds to the standard, i.e. to the taste assessment of the product without addition of flavouring.

TABLE 4

Taste properties of soft drink formulations

|  | C | 1 | 2 | V1 | V2 | V3 |
|---|---|---|---|---|---|---|
| Composition | | | | | | |
| Sucrose | 10 | 7 | 7 | 7 | 7 | 7 |
| Citric acid | 0.2 | 0.2 | 0.2 | 0.2 | 0.2 | 0.2 |
| Steviol glycoside mixture A containing maltodextrins from Example 1 | — | 0.0045 | 0.0045 | — | 0.0045 | — |
| Hesperetin | — | 0.00075 | 0.0012 | — | — | 0.00075 |
| Lemon flavour | 0.1 | 0.1 | 0.1 | 0.1 | 0.1 | 0.1 |
| Water | Ad 100 | | | | | |
| Taste assessment | | | | | | |
| Initial sweetness | 5.7 | 5.2 | 5.2 | 3.2 | 4.2 | 3.2 |
| Sweetness intensity | 6.5 | 5.7 | 5.8 | 3.5 | 4.71 | 3.8 |
| Sugar taste and fullness in the mouth | 5.8 | 4.7 | 5.4 | 3.0 | 4.6 | 3.3 |
| Bitterness in the aftertaste | 0.2 | 0.5 | 0.6 | 0.2 | 0.7 | 0.4 |

The high-sugar control sample C was clearly assessed the best, V1 the poorest. On addition of small amounts of hesperetin alone (V3), all the beneficial flavour values could not be further improved. The steviol glycosides alone (V2) led to improvement in the sweet impression, but also to increased bitterness in the aftertaste. In the case of the embodiments 1 and 2 according to the invention, the initial sweetness, the sweetness intensity and the sugar taste/fullness in the mouth could be again substantially produced comparably to the full sugar variant C, and bitterness in this case markedly decreased in comparison with the pure steviol glycosides (V2).

Example 4

Stability of Drinks

Again, various mixtures of matter based on steviol glycosides were used for producing soft drinks. The products were stored for 48 h at 20° C. and the solubility of the aroma substances was assessed as a function of the concentration of the mixtures according to the invention visually on a scale (0)=completely dissolved, (1)=separate deposits/turbidities and (2)=marked deposits/particle formation. The results are summarized in Table 5.

TABLE 5

Solubility studies

| Composition | 3 | 4 | V4 | V5 |
|---|---|---|---|---|
| Sucrose | 7 | 7 | 7 | 7 |
| Citric acid | 0.2 | 0.2 | 0.2 | 0.2 |

TABLE 5-continued

| Solubility studies | | | | |
|---|---|---|---|---|
| Composition | 3 | 4 | V4 | V5 |
| Steviol glycoside mixture A containing maltodextrins from Example 1 | 0.0045 | 0.0045 | — | 0.0045 |
| Hesperetin | 0.00075 | 0.0012 | — | — |
| Lemon flavour | 0.1 | 0.1 | 0.1 | 0.1 |
| Water | | Ad 100 | | |
| Solubility assessment | | | | |
| After 12 h | 0 | 0 | 1 | 0 |
| After 24 h | 0 | 0 | 2 | 0 |
| After 48 h | 0 | 1 | 2 | 0 |

Embodiment 3 and 4 show, in comparison to Comparative Examples V4 and V5, firstly that the addition of the steviol glycoside/maltodextrin mixture markedly improves the solubility of hesperetin. Also, with respect to the various additional aroma substances, the addition of the mixtures according to the invention improves the solubility.

Hereinafter, the invention will be illustrated on the basis of further formulation examples.

TABLE 6

| Soft drinks (indications of quantity as % by weight) | | | | | | | |
|---|---|---|---|---|---|---|---|
| Ingredients | A | B | C | D | E | F | G |
| Sucrose | 10 | 10 | 7 | — | — | 8 | 7 |
| Glucose/fructose syrup | — | — | — | — | 10 | — | — |
| Steviol glycoside mixture A containing maltodextrins from Example 1 | 0.0045 | 0.005 | 0.003 | 0.01 | 0.0045 | 0.0025 | 0.001 |
| Citric acid | 0.15 | 0.15 | 0.06 | 0.15 | 0.15 | 0.15 | 0.15 |
| Phosphoric acid | — | — | 0.07 | — | — | — | — |
| Caramel colour | — | — | 0.14 | — | — | — | — |
| Caffeine | — | — | 0.01 | — | — | — | — |
| Citrus flavour | 0.1 | 0.05 | — | 0.1 | 0.1 | 0.1 | 0.1 |
| Limonene flavour | — | 0.05 | — | — | — | — | — |
| Drink emulsion of "cola"-type | — | — | 0.05 | — | — | — | — |
| Phloretin | — | — | 0.001 | 0.0005 | — | 0.0005 | 0.01 |
| Hesperetin | 0.00075 | 0.0012 | 0.00075 | 0.0012 | 0.00075 | 0.00075 | 0.01 |
| Homoeriodictyol-Na | — | — | 0.005 | 0.005 | — | — | — |
| Water | | | | Ad 100 | | | |

The ingredients were mixed in the order stated and made up with water to 100%. The mixtures are charged into glass bottles and carbonated.

TABLE 7

| Hard caramels (indications of quantity as % by weight) | | | | |
|---|---|---|---|---|
| Ingredients | A | B | C | D |
| Sugar | 74.50 | — | — | — |
| Palatinit, type M | — | 74.00 | 75.50 | 75.00 |
| Citric acid | 0.5 | 1.0 | 0.5 | — |
| Dye, yellow | — | 0.01 | — | — |
| Dye, red | — | — | 0.01 | — |
| Dye, blue | 0.01 | — | — | 0.01 |
| Peppermint flavour | 0.1 | — | — | 0.1 |
| Citrus flavour | — | 0.1 | — | — |
| Beetroot flavour | — | — | 0.1 | — |
| SWETA[1] | 0.005 | 0.0045 | 0.006 | 0.003 |
| Balansin A | — | 0.005 | 0.010 | 0.005 |
| Hesperetin | 0.00075 | 0.001 | 0.0005 | 0.0004 |

TABLE 7-continued

| Hard caramels (indications of quantity as % by weight) | | | | |
|---|---|---|---|---|
| Ingredients | A | B | C | D |
| Phloretin | — | 0.002 | — | — |
| Water | ad 100 | ad 100 | ad 100 | ad 100 |

[1] Steviol glycoside/maltodextrin mixture (80:20) from Pure Circle

TABLE 8

| Yoghurt with low fat content (indications of quantity as % by weight) | | | | |
|---|---|---|---|---|
| Ingredients | A | B | C | D |
| Sucrose | 10 | 8 | 6 | — |
| Sucralose | — | 0.02 | — | 0.2 |
| Rebaudioside A > 95% | — | — | 0.025 | — |
| Saccharin | — | — | — | 0.3 |
| SWETA[1] | 0.005 | 0.0045 | 0.01 | 0.050 |
| Sour cherry extract according to Example 1 | 0.2 | 0.1 | 0.2 | 0.2 |
| Hesperetin | 0.00075 | 0.001 | 0.003 | 0.002 |
| Phloretin | — | — | 0.002 | 0.002 |
| Homoeriodictyol-sodium salt | — | — | — | 0.005 |
| Yoghurt, 0.1% fat | | make up to 100% | | |

TABLE 9

| Fruit gums (indications of quantity as % by weight) | | |
|---|---|---|
| Ingredients | A | B |
| Sucrose | 34.50 | 8.20 |
| Glucose syrup, DE 40 | 31.89 | 30.09 |
| SWETA[1] | 0.005 | 0.0045 |
| Iso syrup C* Tru Sweet 01750 (Cerestar GmbH) | 1.50 | 2.10 |
| Gelatin 240 Bloom | 8.20 | 9.40 |

TABLE 9-continued

Fruit gums (indications of quantity as % by weight)

| Ingredients | A | B |
|---|---|---|
| Polydextrose (Litesse ® Ultra, Danisco Cultor GmbH) | — | 24.40 |
| Dye | 0.01 | 0.01 |
| Citrus flavour | 0.20 | — |
| Cherry flavour | — | 0.10 |
| Hesperetin | 0.0075 | 0.0015 |
| Water | ad 100 | ad 100 |

TABLE 10

Sugar-free chewing gum (indications of quantity as % by weight)

| Ingredients | Content |
|---|---|
| Chewing gum base | 30.00 |
| Sorbitol powder | Ad 100 |
| SWETA[1) ] | 0.05 |
| Palatinit | 9.50 |
| Xylitol | 2.00 |
| Mannitol | 3.00 |
| Aspartame | 0.10 |
| Acesulfame K | 0.10 |
| Emulgum/emulsifier | 0.30 |
| Sorbitol 70%. in water | 14.00 |
| Glycerol | 1.00 |
| Peppermint flavour | 1.50 |
| Hesperetin | 0.01 |

TABLE 11

Pudding (indications of quantity in g)

| Ingredients | A | B | C |
|---|---|---|---|
| Corn starch | 38 | 38 | 38 |
| Sugar | 38 | 30 | 22.8 |
| Steviol glycosides | — | 0.05 | 0.08 |
| Hesperetin | — | 0.01 | 0.03 |
| Vanilla flavour (Symrise) | 0.2 | 0.2 | 0.2 |
| Quinoline yellow | 0.02 | 0.02 | 0.02 |
| Milk | 500 ml | 500 ml | 500 ml |

What claimed is:

1. A mixture of matter comprising:
 (a) from 5 to 50 wt. %, based on the total weight of the mixture of matter, of a steviol glycoside composition, the steviol glycoside composition comprising:
  (a1) about 1 to about 50 wt. % of rebaudioside A, isomers thereof, or a mixture thereof;
  (a2) about 0.1 to about 30 wt. % of rebaudioside B, isomers thereof, or a mixture thereof;
  (a3) about 1 to about 50 wt. % of rebaudioside C, isomers thereof, or a mixture thereof;
  (a4) about 1 to about 25 wt. % of rebaudioside D, isomers thereof, or a mixture thereof;
  (a5) about 1 to about 5 wt. % of stevioside, isomers thereof, or a mixture thereof; and
  (a6) about 1 to about 5 wt. % of steviolbioside, isomers thereof, or a mixture thereof;
   wherein the weight percentages of (a1)-(a6) are based on the total weight of the steviol glycoside composition;
 (b) from 0.1 to 15 wt. %, based on the total weight of the mixture of matter, of maltodextrin, and
 (c) from 0.1 to 20 wt. %, based on the total weight of the mixture of matter, of one or more phenolic sweetness-enhancing aroma substances selected from the group consisting of:

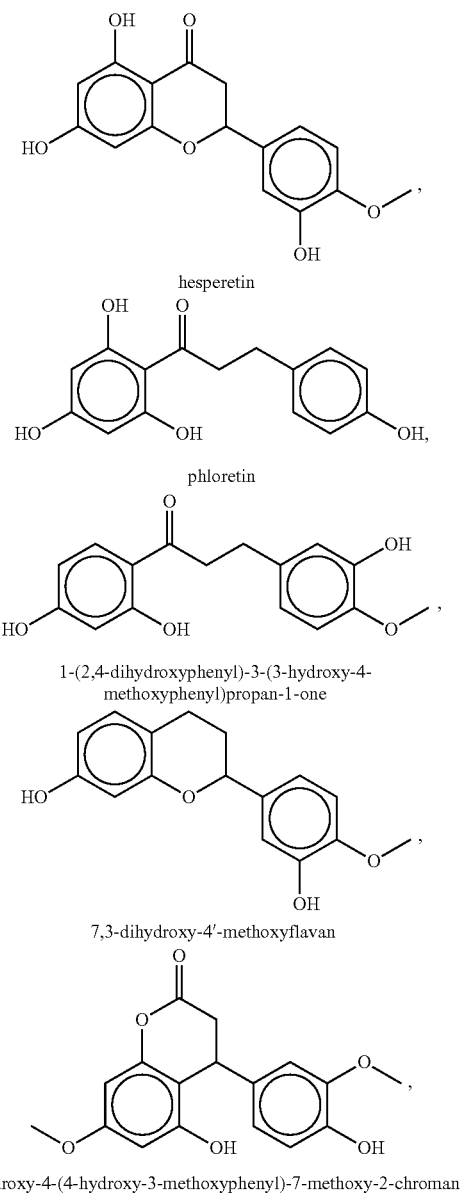

and a mixture thereof;
 wherein,
  the weight ratio of (a+b) to (c) is from about 3:1 to about 6:1;
  the mixture of matter improves the taste of the (a) steviol glycoside composition compared to an otherwise identical mixture of matter lacking the (c) one or more phenolic sweetness-enhancing aroma substances, and
  the mixture of matter improves the solubility of the (c) one or more phenolic sweetness-enhancing aroma substances in water compared to an otherwise identical mixture of matter lacking the (a) steviol glycoside composition and the (b) maltodextrin.

2. The mixture of matter of claim 1, wherein the weight ratio of the (a) steviol glycoside composition to the (b) maltodextrin is 60:40 to 90:10.

3. The mixture of matter of claim 1, wherein the weight ratio of the (a) steviol glycoside composition to the (b) maltodextrin is 70:30 to 80:20.

4. The mixture of matter of claim 1, wherein the steviol glycoside composition comprises:
(a1) 30 to 50% by weight rebaudioside A, isomers thereof, or a mixture thereof,
(a2) 5 to 10% by weight rebaudioside B, isomers thereof, or a mixture thereof,
(a3) 5 to 10% by weight rebaudioside C, a isomers thereof, or a mixture thereof,
(a4) 20 to 30% by weight rebaudioside D, isomers thereof, or a mixture thereof,
(a5) 15 to 25% by weight stevioside, isomers thereof, or a mixture thereof, and
(a6) 1 to 5% by weight steviolbioside, isomers thereof, or a mixture thereof.

5. The mixture of matter of claim 1, wherein the (c) of one or more phenolic sweetness-enhancing aroma substances are selected from the group consisting of hesperitin, phloretin, and a mixture thereof.

6. The mixture of matter of claim 4, wherein the (c) of one or more phenolic sweetness-enhancing aroma substances are selected from the group consisting of hesperitin, phloretin, and a mixture thereof.

7. A preparation for oral consumption comprising from 0.00001 to 2 wt. % of the mixture of matter of claim 1, based on the total weight of the preparation for oral composition.

8. The preparation of claim 7, wherein the preparation is an alcoholic or non-alcoholic beverage.

9. The beverage of 8 further containing sweeteners, food acids, acidity regulators, thickeners and additional aroma substances.

10. A method for optimizing the taste of a preparation for oral consumption comprising adding from 0.0001 to 2% by weight, based on the total weight of the preparation, of the mixture of matter of claim 1 to the preparation.

11. A method for enhancing aroma of a preparation for oral consumption comprising adding the mixture of matter of claim 1 as an aroma substance to the preparation.

12. A method for enhancing solubility of aroma substance comprising adding the mixture of claim 1 as solubility enhancer to the aroma substance.

13. A mixture of matter comprising:
(a) from 5 to 50 wt. %, based on the total weight of the mixture of matter, of a steviol glycoside composition, the steviol glycoside composition comprising:
(a1) about 1 to about 50 wt. % of rebaudioside A, isomers thereof, or a mixture thereof;
(a2) about 0.1 to about 30 wt. % of rebaudioside B, isomers thereof, or a mixture thereof;
(a3) about 1 to about 50 wt. % of rebaudioside C, isomers thereof, or a mixture thereof;
(a4) about 1 to about 25 wt. % of rebaudioside D, isomers thereof, or a mixture thereof;
(a5) about 1 to about 5 wt. % of stevioside, isomers thereof, or a mixture thereof; and
(a6) about 1 to about 5 wt. % of steviolbioside, isomers thereof, or a mixture thereof;
wherein the weight percentages of (a1)-(a6) are based on the total weight of the steviol glycoside composition;
(b) from 0.1 to 15 wt. %, based on the total weight of the mixture of matter, of maltodextrin, and
(c) from 0.1 to 20 wt. %, based on the total weight of the mixture of matter, of hesperetin:

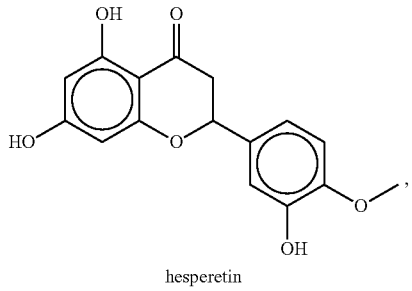

hesperetin wherein,
the weight ratio of (a+b) to (c) is from about 3:1 to about 6:1;
the mixture of matter improves the taste of the (a) steviol glycoside composition compared to an otherwise identical mixture of matter lacking the (c) hesperetin, and
the mixture of matter improves the solubility of the (c) hesperetin in water compared to an otherwise identical mixture of matter lacking the (a) steviol glycoside composition and the (b) maltodextrin.

14. The mixture of matter of claim 13, wherein the weight ratio of the (a) steviol glycoside composition to the (b) maltodextrin is 60:40 to 90:10.

15. The mixture of matter of claim 13, wherein the weight ratio of the (a) steviol glycoside composition to the (b) maltodextrin is 70:30 to 80:20.

16. The mixture of matter of claim 13, wherein the steviol glycoside composition comprises:
(a1) 30 to 50% by weight rebaudioside A, isomers thereof, or a mixture thereof,
(a2) 5 to 10% by weight rebaudioside B, isomers thereof, or a mixture thereof,
(a3) 5 to 10% by weight rebaudioside C, isomers thereof, or a mixture thereof,
(a4) 20 to 30% by weight rebaudioside D, isomers thereof, or a mixture thereof,
(a5) 15 to 25% by weight stevioside, isomers thereof, or a mixture thereof, and
(a6) 1 to 5% by weight steviolbioside, isomers thereof, or a mixture thereof.

17. A preparation for oral consumption comprising from 0.00001 to 2 wt. % of the mixture of matter of claim 13, based on the total weight of the preparation for oral composition.

18. A method for optimizing the taste of a preparation for oral consumption comprising adding from 0.0001 to 2% by weight, based on the total weight of the preparation, of the mixture of matter of claim 13 to the preparation.

* * * * *